United States Patent
Boone et al.

(10) Patent No.: US 10,975,425 B2
(45) Date of Patent: Apr. 13, 2021

(54) RAPID NUCLEIC ISOLATION METHOD AND FLUID HANDLING DEVICES

(71) Applicant: UNITED STATES OF AMERICA AS REPRESENTED BY THE ADMINISTRATOR OF NASA, Washington, DC (US)

(72) Inventors: Travis David Boone, Mountain View, CA (US); Jimmy Kar Chuen Jung, Mountain View, CA (US); Macarena Parra, Gilroy, CA (US); Mark Brown, Yorba Linda, CA (US)

(73) Assignee: United States of America as Represented by the Administrator of NASA, Washington, DC (US)

( * ) Notice: Subject to any disclaimer, the term of this patent is extended or adjusted under 35 U.S.C. 154(b) by 379 days.

(21) Appl. No.: 15/688,765

(22) Filed: Aug. 28, 2017

(65) Prior Publication Data
US 2019/0062802 A1 Feb. 28, 2019

(51) Int. Cl.
| | |
|---|---|
| C12Q 1/68 | (2018.01) |
| C12N 15/10 | (2006.01) |
| C12Q 1/686 | (2018.01) |
| B01D 61/18 | (2006.01) |
| C12N 15/09 | (2006.01) |
| C12P 19/34 | (2006.01) |
| G01N 33/53 | (2006.01) |
| G05D 7/06 | (2006.01) |
| C12Q 1/6806 | (2018.01) |

(52) U.S. Cl.
CPC ............. *C12Q 1/686* (2013.01); *B01D 61/18* (2013.01); *C12N 15/09* (2013.01); *C12N 15/1003* (2013.01); *C12P 19/34* (2013.01); *C12Q 1/6806* (2013.01); *G01N 33/53* (2013.01); *G05D 7/0629* (2013.01)

(58) Field of Classification Search
CPC ...... C12Q 1/686; C12Q 1/6806; C12N 15/09; C12N 15/1003; G01N 33/53
See application file for complete search history.

(56) References Cited

U.S. PATENT DOCUMENTS

| | | | | |
|---|---|---|---|---|
| 2010/0112667 | A1* | 5/2010 | Sundaram | C12M 47/06 435/235.1 |
| 2012/0107912 | A1* | 5/2012 | Hwang | C12M 47/06 435/235.1 |
| 2012/0252008 | A1* | 10/2012 | Brown | C12M 47/06 435/6.1 |
| 2013/0295652 | A1* | 11/2013 | Zhang | B01L 3/502738 435/270 |

OTHER PUBLICATIONS

Amelia Williamson Smith, "WETLAB-2: Transforming the ISS into a Living Laboratory," Upward Magazine, Issue 3, pp. 5 and 6 (Sep. 27, 2016).
Claremont Bio PureLyse Binding Buffer Material Data Safety Sheet (Jun. 20, 2011).
Claremont Bio PureLyse Elution Buffer Material Data Safety Sheet (Jun. 20, 2011).

* cited by examiner

*Primary Examiner* — Jezia Riley
(74) *Attorney, Agent, or Firm* — Rhys W. Cheung; Robert M. Padilla; Helen M. Galus

(57) ABSTRACT

A novel assay and a suite of devices may isolate nucleic acids from prokaryotic and eukaryotic cells and prepare samples for real-time (quantitative) polymerase chain reaction (PCR) analysis. The assay may employ an aqueous-based non-alcohol approach that yields robust RNA quality. The suite of ready-to-use devices may provide pre-loaded reagents in liquid and lyophilized formats to enable rapid manual operation in a laboratory or remote field environments. The assay and devices may be particularly suitable to analysis in microgravity or deep space environments.

20 Claims, 5 Drawing Sheets

RAPID NUCLEIC ISOLATION METHOD AND FLUID HANDLING DEVICES

ORIGIN OF THE INVENTION

The invention described herein was made in the performance of work under NASA contracts and is subject to the provisions of 51 U.S.C. § 20135(b) Public Law 111-314, § 3(124 Stat. 3330, 51 U.S.C. Chapter 201), and 35 U.S.C. § 202 Public Law 96-517, and may be manufactured and used by or for the Government for governmental purposes without the payment of any royalties thereon or therefore. In accordance with 35 U.S.C. § 202, the contractor has elected not to retain title.

FIELD

The present invention generally pertains to extraction, capture, and elution of biological material and lysing of the biological material, and more specifically, to extraction, capture, and elution of biological material from biological specimens using particulate materials and lysing of the biological material using a lysing particulate material in a fully enclosed system.

BACKGROUND

Lysis of biological specimens (e.g., cell lysis) is used to provide biological materials for compositional analysis. Specific biological materials may include proteins, lipids, and nucleic acids, either individually or as complexes. When a cell membrane is lysed, certain organelles (nuclei, mitochondria, lysosomes, chloroplasts, and/or endoplasmic reticula) may be isolated. These organelles may be analyzed using suitable techniques, such as polymerase chain reaction (PCR), electron microscopy, Western blotting, or other analysis techniques.

Various approaches exist for performing lysis. For example, enzymatic approaches may be employed to remove cell walls using appropriate enzymes in preparation for cell disruption or to prepare protoplasts. Another approach employs detergents to chemically disrupt cell membranes. These chemical approaches may adversely affect the resulting product. For example, they may degrade the bioproducts being released. Consequently, chemical approaches may, in some instances, not be practical.

Yet another approach employs ultrasound to produce cavitation and impaction for disrupting the cells. However, this approach may not achieve as high a lysis efficiency as may be required or desired for many applications. Still another approach employs beads (e.g., made from glass or ceramic material) that are agitated via a vortex mixer, for example. This approach successfully addresses the issues raised by chemical lysis approaches, yet improvements in this approach are still desirable.

Particular biological materials that are isolated from the interior of cells or viruses for use in a variety of analysis or testing procedures include nucleic acids. These biological materials may be isolated and used, for example, in testing for bacterial or viral infections. Nucleic acid analysis or testing for such purposes may provide improved sensitivity or may shorten the time between incidence of an infection and appearance of a positive test, as compared to results obtained from more traditional antibody testing. Nucleic acid analysis or testing typically involves extraction and isolation of a nucleic acid of interest (e.g., deoxyribonucleic acid (DNA) or ribonucleic acid (RNA)) from the biological specimens, followed by amplification reactions, such as PCR. Amplification of the isolated nucleic acid increases the sensitivity of detection and identification of the resulting nucleic acid.

Commonly used techniques for rapid extraction and isolation of nucleic acids from cells, and in particular, DNA or RNA, utilize membranes or beads (including magnetic beads) that are made from silica or from other materials that capture DNA or RNA nonspecifically on the basis of the polyanionic chemistry of DNA or RNA. However, most such techniques rely on the use of harsh reagents. Indeed, ribonucleic acid (RNA) isolation for genomic research has traditionally been accomplished using alcohol, chaotropic salts (e.g., guanidinium hydrochloride, guanidinium thiocyanate, or proteases), and a centrifuge to lyse cells to free the DNA or RNA. Alcohol is a fire hazard for space flight and interferes with the environmental control and life support system (ECLSS) functionality. Also, chaotropic salts are hazardous. As such, samples had to be returned to Earth to safely perform analysis.

The harsh reagents used in such methods of DNA or RNA isolation are not compatible with subsequent amplification reactions. The reagents should thus be thoroughly removed, often by numerous wash steps, prior to elution and subsequent use or analysis of the isolated DNA or RNA. Even the wash steps may include reagents that are incompatible with subsequent reactions, and should thus be removed. For example, washes may include alcohol, which should then be removed by evaporation. Also, deoxyribonucleic acid (DNA) contamination should be removed prior to polymerase chain reaction (PCR) analysis to avoid false positive signals from DNA versus RNA templates. Furthermore, centrifuge operations typically require fluid transfers that are challenging to achieve with the containment required for fluid handling in space. Accordingly, an improved approach to nucleic acid isolation and fluid handling may be beneficial.

SUMMARY

Certain embodiments of the present invention may provide solutions to the problems and needs in the art that have not yet been fully identified, appreciated, or solved by conventional assay technologies. For example, some embodiments of the present invention pertain to a novel assay and a suite of devices to isolate nucleic acids from prokaryotic and eukaryotic cells and prepare samples for real-time (quantitative) PCR analysis. The assay of some embodiments employs an aqueous-based non-alcohol approach that yields robust RNA quality. The suite of ready-to-use devices may provide pre-loaded reagents in liquid and lyophilized formats to enable rapid manual operation in a laboratory or remote field environments.

Some embodiments provide a method of isolating nucleic acid that includes contacting a specimen containing a nucleic acid with a particulate material having an affinity for the nucleic acid to allow at least a portion of the nucleic acid to bind to the particulate material and washing the particulate material having the bound nucleic acid with a low ionic strength zwitterion-containing buffer to yield a washed particulate material having the nucleic acid bound thereto. Contacting a specimen containing a nucleic acid with a particulate material may include contacting the specimen with a plurality of particles comprising at least one of a ceramic, a glass, a zirconia, a silica, a sand, or a metal core coated by a material that facilitates binding of the nucleic acid. The specimen may include a binding medium. Contacting a specimen containing a nucleic acid with a particulate material may include contacting the specimen including the binding medium with the particulate material. The binding medium may include a composition that induces binding of the nucleic acid to the particulate material. Washing the particulate material with a low ionic strength zwitterion-containing buffer may include washing the particulate material with a low ionic strength zwitterion-containing buffer having a pH between 3 and 6. Washing the particulate material with a low ionic strength zwitterion-containing buffer may include washing the particulate material with a buffer comprising one or more of an amino acid, an aminosulfonic acid, or an aminocarboxylic acid. Washing the particulate material with a low ionic strength zwitterion-containing buffer may include washing the particulate material with a buffer comprising at least one zwitterionic substance having a pKa within a range between 2 and 4. The low ionic strength zwitterion-containing buffer may be a glycine buffer at approximately pH 4.

The method of some embodiments may further include applying to the washed particulate material a low ionic strength buffer having a pH that will adjust the pH at the surface of the particulate. A formulation for use in isolating nucleic acid by a particulate material may be summarized as including a low ionic strength zwitterion-containing buffer having a pH less than 6 to induce binding of nucleic acid to or to prevent release of bound nucleic acid from the particulate material. The low ionic strength zwitterion-containing buffer may have a pH between 3 and 6. The low ionic strength zwitterion-containing buffer may include a zwitterionic substance having a pKa between 2 and 4. The low ionic strength zwitterion-containing buffer may include a zwitterionic substance having a pKb between 9 and 11. The low ionic strength zwitterion-containing buffer may include a zwitterionic substance that is an amino acid, an aminosulfonic acid, or an aminocarboxylic acid. The low ionic strength zwitterion-containing buffer may be a glycine buffer having a pH of approximately 4.

A kit for use in lysis cells and isolating nucleic acid may include a lysing device containing particulate lysing material for mechanically lysing cells in a biological sample and a column or chamber attached to or having the ability to be attached to the outlet of the lysing device containing a particulate material that has an affinity for nucleic acid. The kit may also include a low ionic strength zwitterion-containing buffer having a pH less than 6, an elution buffer having a pH greater than 7, and instructions for use of the kit to lyse and isolate nucleic acid. The low ionic strength zwitterion-containing buffer may have a pH between 3 and 6. The elution buffer may have a pH of between 8 and 9.5.

A kit for use in microgravity environments for lysing cells and isolating nucleic acid may include a low ionic strength zwitterion-containing buffer having a pH less than 6 in a fully enclosed chamber, an elution buffer having a pH greater than 7 in a fully enclosed chamber, and instructions for use of the kit to lyse and isolate nucleic acid in a fully enclosed system. The low ionic strength zwitterion-containing buffer may have a pH between 3 and 6. The elution buffer may have a pH of between 8 and 9.5. The low ionic strength zwitterion-containing buffer may include a zwitterionic substance that is an amino acid, an aminosulfonic acid, or an aminocarboxylic acid.

In an embodiment, a method of extracting and purifying a biological sample using a sample preparation device includes pumping a sample solution including a biological sample and a binding buffer into a lysis chamber. The binding buffer does not include a chaotropic salt. The method also includes lysing the sample solution in the lysis chamber to break down biological components of the biological sample and pumping the lysed sample solution from the lysis chamber through an extraction column and into a waste chamber. The method further includes washing the sample preparation device using at least one wash buffer by pumping the at least one wash buffer into and out of the lysis chamber, through the extraction column, and into the waste chamber. The at least one wash buffer does not include alcohol. Additionally, the method includes performing at least one elution using at least one elution buffer to properly extract DNA, RNA, or a protein from the extraction column and collecting the extracted DNA, RNA, or protein.

In another embodiment, a method includes pumping a sample solution including a biological sample and a binding buffer into a lysis chamber. The binding buffer does not include a chaotropic salt. The method also includes lysing the sample solution in the lysis chamber to break down biological components of the biological sample and pumping the lysed sample solution from the lysis chamber through an extraction column and into a waste chamber. The method further includes washing the sample preparation device using at least one wash buffer by pumping the at least one wash buffer into and out of the lysis chamber, through the extraction column, and into the waste chamber. The at least one wash buffer does not include alcohol. Additionally, the method includes performing at least one elution using at least one elution buffer to properly extract DNA, RNA, or a protein from the extraction column and collecting the extracted DNA, RNA, or protein.

In yet another embodiment, a method includes lysing a sample solution in a lysis chamber of a sample preparation device to break down biological components of a biological sample including a binding buffer. The binding buffer does not include a chaotropic salt. The method also includes washing the sample preparation device using at least one wash buffer by pumping the at least one wash buffer into and out of the lysis chamber, through an extraction column, and into a waste chamber. The at least one wash buffer does not include alcohol.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE EMBODIMENTS

Figure 1:
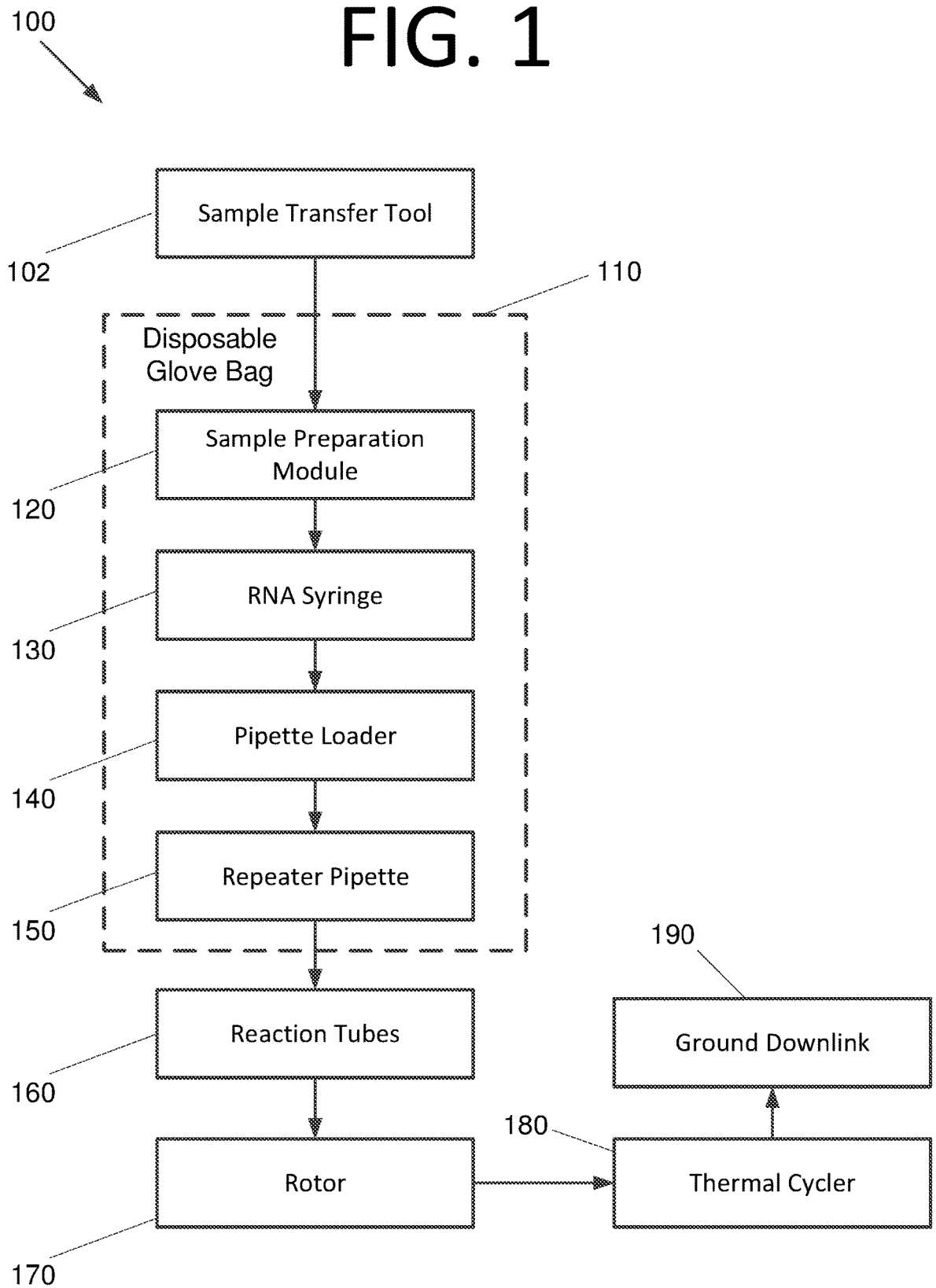
FIG. 1 is a flow diagram illustrating a sample lysing, capture, elution, and analysis process, according to an embodiment of the present invention.

Some embodiments of the present invention pertain to a novel assay and a suite of devices to isolate nucleic acids from prokaryotic and eukaryotic cells and prepare samples for real-time (quantitative) polymerase chain reaction (PCR) analysis. The assay of some embodiments employs an aqueous-based non-alcohol approach that yields robust RNA quality. The suite of ready-to-use devices may provide pre-loaded reagents in liquid and lyophilized formats to enable rapid manual operation in a laboratory or remote field environments.

Such embodiments may be particularly suitable to analysis in microgravity or deep space environments. However, embodiments are not limited to microgravity or deep space applications, and may be employed for terrestrial purposes as well. Some embodiments may be fully enclosed so that material within the system, such as fluids and cells, are not released into the environment (e.g., internal compartments of a space vehicle). Some embodiments may also provide the benefits of rapidly lysing cells and isolating RNA for analysis. For example, total RNA isolation may be provided in order to perform gene expression analysis of biological samples.

Certain embodiments may provide particle-based or other solid phase systems and processes that efficiently obtain biological material. Such improved systems and processes may reduce the amount of time required to process a sample (i.e., a sample from which to obtain the biological material) and/or to increase throughput. Such systems and processes may also increase the degree of thoroughness of obtaining the material, yielding greater amounts of material from a given sample size.

Some embodiments also provide systems and processes for lysis, capture, and elution of biological material without separate processing of particles on which the biological material is captured. In particular, lysis, capture, and elution of biological materials may be provided within the same system by controlling chemical composition and flow of reagents within the system. Lysing of cells without use of harsh reagents is also beneficial. This may avoid wash steps during processing of biological material captured by particle-based systems. Furthermore, processes and formulations for more efficiently processing particle-bound or other solid phase-bound biological materials produced by conventional approaches may be beneficial.

Use of solid phase materials and methods for specific capture of cells or cell components may be beneficial. For example, efficiently isolating and processing microorganisms having cell walls with high lipid content, such as mycobacteria, may be beneficial. Materials and processes for more efficient and effective removal of contaminating substances from biological materials isolated for further analysis may also be beneficial. For example, materials and processes of some embodiments may remove biological contaminants that may interfere with subsequent analysis or otherwise limit the sensitivity of analysis of biological materials of interest, such as DNA or RNA. Sample heating may be integrated within a system in some embodiments. Equipment of some embodiments is small, portable, and relatively inexpensive, yet sufficiently robust to withstand travel or harsh operating environments.

Some embodiments of the present invention are, or use, fully enclosed or fully contained sample preparation devices such that the inner surfaces of the devices are never exposed to the environment outside the device and the environment outside the device is never exposed to the components and/or materials including the inner portions of the device or to any fluids contained in the device or are injected into the device. Such containment is important, particularly when such devices and methods are used onboard space vehicles where gravity is reduced compared to the gravity on the surface of the Earth (i.e., a microgravity environment). In such microgravity environments, fluids cannot easily be contained in open vessels and any fluids which are not fully contained are difficult to capture and remove from the environment of the space vehicle.

Microgravity environments, as used herein, include any environment where the gravity is less than the gravity on the surface of Earth. Examples include, but are not limited to, onboard space vehicles orbiting the Earth, or in transit to another planet or other object orbiting the Earth, sun, or another planet, or moon. Another example is onboard aircraft that are rapidly accelerating toward the Earth (free fall) such that the force of the Earth's gravity is countered by the acceleration force toward the Earth, reducing the net gravity experienced on the aircraft.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well known structures associated with micromotors, controllers including motor controllers, and control systems such as programmed general purpose computing systems and the like have not been shown or described in detail to avoid unnecessarily obscuring descriptions of the embodiments. In other instances, methods commonly known for use with and manipulation of nucleic acids, proteins, polypeptides, and other biological materials have not been described as they would be readily available to those of ordinary skill in the art of such materials. Such common methods include, for example, PCR and heat denaturation of DNA or RNA.

The material to be lysed may take the form of biological materials including, but not limited to, cells, spores, tissue, yeast, fungi, plants, bacteria, etc. The biological materials may typically be suspended in a liquid medium. The lysing particulate material may take a variety of forms. While often referred to herein as beads, the term "bead" is not meant to be limiting with respect to size or shape. The beads may include, for example, a ceramic, a glass, zirconia, zirconia/silica, zirconium silicate, yttria-stabilized zirconia, metal, plastic, nickel, tungsten, and/or tungsten carbide, yttrium-stabilized zirconia, sand, and/or particles of any geometry, such as shard or of random shape. The lysed material may also take a variety of forms including, but not limited to, nucleic acids, polypeptides, proteins, organelles-nuclei, mitochondria, lysosomes, chloroplasts, endoplasmic reticula, etc. Biological specimens, such as cells or viruses, may be lysed by mechanical disruption in a lysing chamber containing particulate material, for example beads made from silica and/or zirconia. The volume of the lysing chamber may be crowded with the particulate material.

The particulate material in the lysing chamber may be driven rapidly by an impeller connected to a small motor to lyse the biological specimens. The motor may be disposable. Alternatively, the lysing chamber may be oscillated to drive the particulate material to lyse the biological specimens.

Further, treatment of the contents of the lysing chamber may include ultrasonic treatment. Such different types of mechanical disruption allow lysis to occur without the use of harsh chemicals, such as chaotropic agents. In comparison to standard procedures for preparation of biological materials, the procedures disclosed herein may save time by eliminating wash steps that are typically included to remove harsh chemicals. Chemical conditions within the lysing chamber may be controlled during lysis to allow simultaneous lysis of the biological specimen and binding or collection of the biological material released by lysis on the particulate material. As another alternative, the particulate lysing material may be agitated using ultrasonic energy delivered by an ultrasonic horn separate from the lysis chamber but in contact with it to achieve efficient transfer of the ultrasonic energy to the lysis chamber.

Some embodiments advantageously allow relatively simple, efficient approaches to lysis, capture, and elution of biological materials from biological specimens. The surprisingly advantageous approaches may involve appropriately timed, simple control of flow direction and chemical compositions of fluids within a lysing system. The biological material, e.g., DNA or RNA, may then be subjected to testing or analysis or used for other purposes. The absence of harsh reagents during lysis may not only save time but also yield materials that are more suitable for use in subsequent procedures. Thus, the disclosed systems and methods provide rapid and efficient lysis of specimens, e.g., cells, and capture of biological materials, e.g., DNA or RNA, in a single chamber by sequential use of fluids having chemical compositions particularly appropriate for lysis, capture and elution.

Some embodiments may allow for analyte capture through various mechanisms either within the same chamber in which lysis occurs and/or in other chambers, for instance chambers arranged subsequently with respect to a flow of sample or specimen. This approach still advantageously obviates the use of harsh reagents, as well as eliminating the associated need to perform wash acts or steps prior to any subsequent enzymatic reaction. For example, 1 µm magnetic particles can be combined with the sample or specimen before or after disruption (i.e., lysing). Thus, DNA or RNA capture can occur on these magnetic particles after the disruption has been accomplished by larger lysing particulate or beads. This principle may also be applied to other non-chemical approaches to cell lysis, such as sonication, where capture may occur on an additional surface at the same time or following sonication. This may still allow wash acts or steps to be avoided before any enzymatic reaction.

FIG. 1 is a flow diagram illustrating a sample lysing, capture, elution, and analysis process 100, according to an embodiment of the present invention. The first step in this embodiment is to transfer a biological sample, via a sample transfer tool 102 (e.g., a syringe or pipette), to a sample preparation module 120. In this embodiment, sample preparation module 120, an RNA syringe 130, a pipette loader 140, and a repeater pipette 150 are all used within a disposable glove bag 110 to avoid contamination of the RNA by individuals involved in the process.

Sample preparation module 120 extracts and purifies a nucleic acid (in this case, RNA). More specifically, sample preparation module 120 performs lysis, capture, and elution of the RNA. RNA syringe 130 is then used to remove the purified RNA liquid. However, when the liquid is removed, some air is typically removed with it, creating air bubbles that can be difficult to separate from the liquid without sufficient gravity to keep them at the top. As such, holding RNA syringe 130 upright and tapping it does not release the bubbles. Also, this tapping process does not work in microgravity. To address this problem, RNA syringe 130 is used to inject the liquid into pipette loader 140, which removes the bubbles.

Repeater pipette 150 is then used to remove the now airless liquid from pipette loader 140 and load it into reaction tubes 160, which contain freeze-dried materials for RT-qPCR. For RT-qPCR, the RNA must be combined with several components. In a ground-based lab, an investigator walks around the lab to collect all of the components that are needed. Because this is not plausible in microgravity, this embodiment uses a novel freeze-dried bead to put in the bottom of each reaction tube containing everything needed for RT-qPCR. Reaction tubes 160 are then loaded into a rotor 170 that may attach to a drill or any other suitable motorized device that provides rotation. To rehydrate the freeze-dried bead, the RNA liquid must get to the bottom of the reaction tubes. However, the liquid does not immediately fall to the bottom of the tubes. Thus, rotor 170 holds the tubes and may attach to the tip of a hand-held drill, for instance, allowing an experimenter to use the drill to spin the tubes and bring the liquid down. Rotor 170 is then spun to bring the liquid to the bottom of reaction tubes 160 and to rehydrate the freeze-dried materials.

Once reaction tubes 160 are activated via rotor 170, reaction tubes 160 are loaded into a thermal cycler 180 to perform RT-qPCR. Reverse transcription converts the RNA to DNA, the DNA is amplified to detect gene expression, and the gene expression is quantitatively measured using fluorescent probes. The results of the RT-qPCR are then sent to the ground using data downlink 190.

Figure 2:
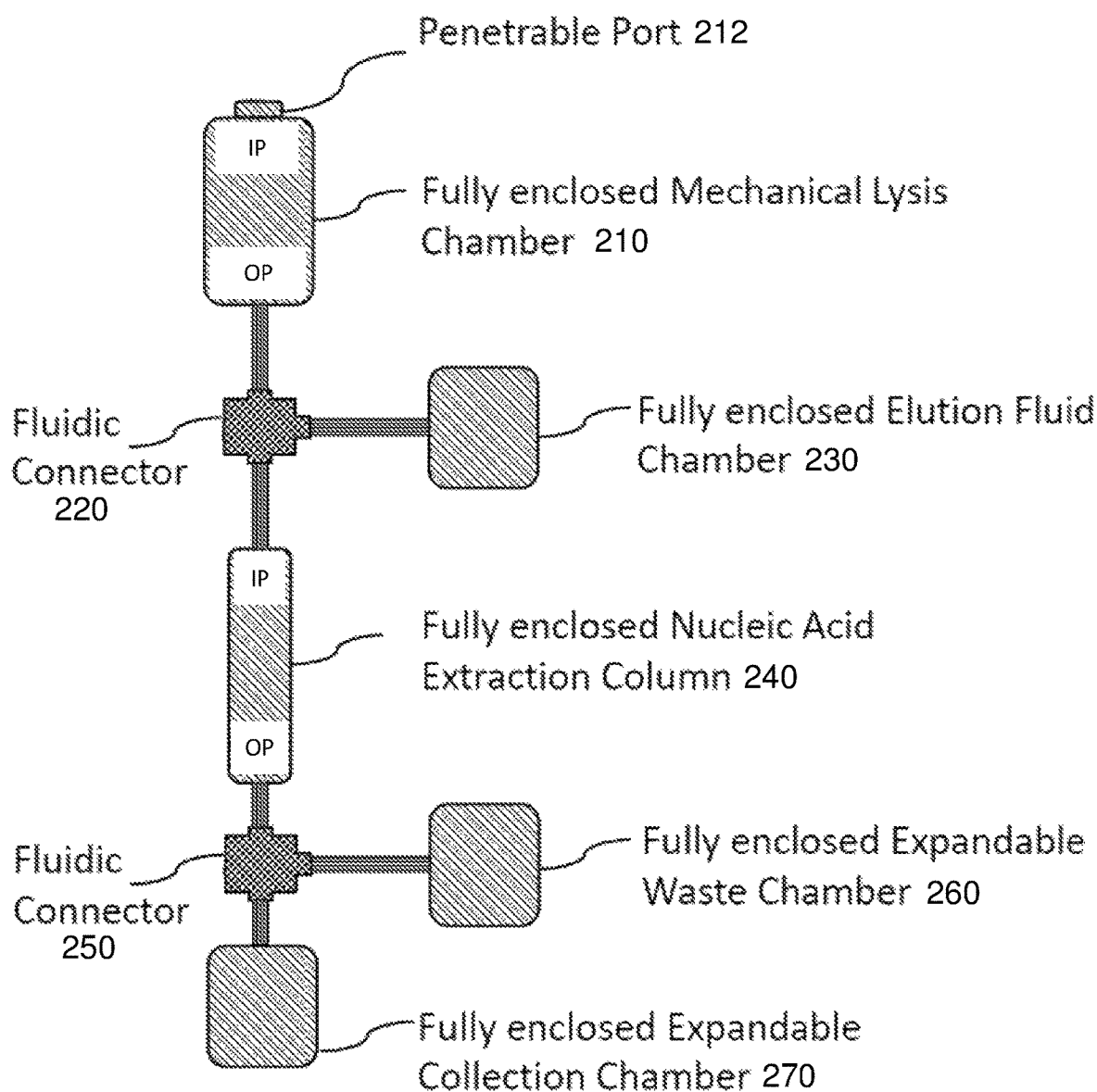
FIG. 2 is an architectural diagram illustrating a fully enclosed sample preparation device, according to an embodiment of the present invention.

FIG. 2 is an architectural diagram illustrating a fully enclosed sample preparation device 200, according to an embodiment of the present invention. In some embodiments, sample preparation device 200 may be sample preparation module 120 of FIG. 1. Fully enclosed sample preparation device 200 performs lysis (via mechanical disruption in this embodiment), capture (i.e., binding of DNA, RNA, or protein to a particulate), and elution (i.e., extracting the pure DNA, RNA, or protein) of the biological sample, which is contained within an extraction fluid.

Sample preparation device 200 includes a fully enclosed mechanical lysis chamber 210 that contains a particulate lysing material. An inlet port (IP) of fully enclosed mechanical lysis chamber 210 is sealed with a penetrable port 212 capable of passing fluid into fully enclosed mechanical lysis chamber 210 while maintaining a fully enclosed state of fully enclosed sample preparation device 200. An outlet port (OP) of fully enclosed mechanical lysis chamber 210 is sealably connected via a first fluidic connector 220 to an inlet port (IP) of a fully enclosed nucleic acid extraction column 240. Fully enclosed elution fluid chamber 230 is also connected to first fluidic connector. Fully enclosed elution fluid chamber 230 contains an elution fluid that facilitates elution of the nucleic acid of interest.

Fully enclosed nucleic acid extraction column 240 includes an affinity medium (e.g., a particulate) having an affinity for the nucleic acid. An outlet port (OP) of fully enclosed nucleic acid extraction column 240 is sealably connected via a second fluidic connector 250 to a fully enclosed expandable waste chamber 260 and a fully enclosed expandable collection chamber 270. In some embodiments, the various components of sample preparation device 200 may be combined in a monolithic fashion— for example, in a single block of plastic. Thus, sample preparation device 200 may be 3D printed in some embodiments.

Figure 3:
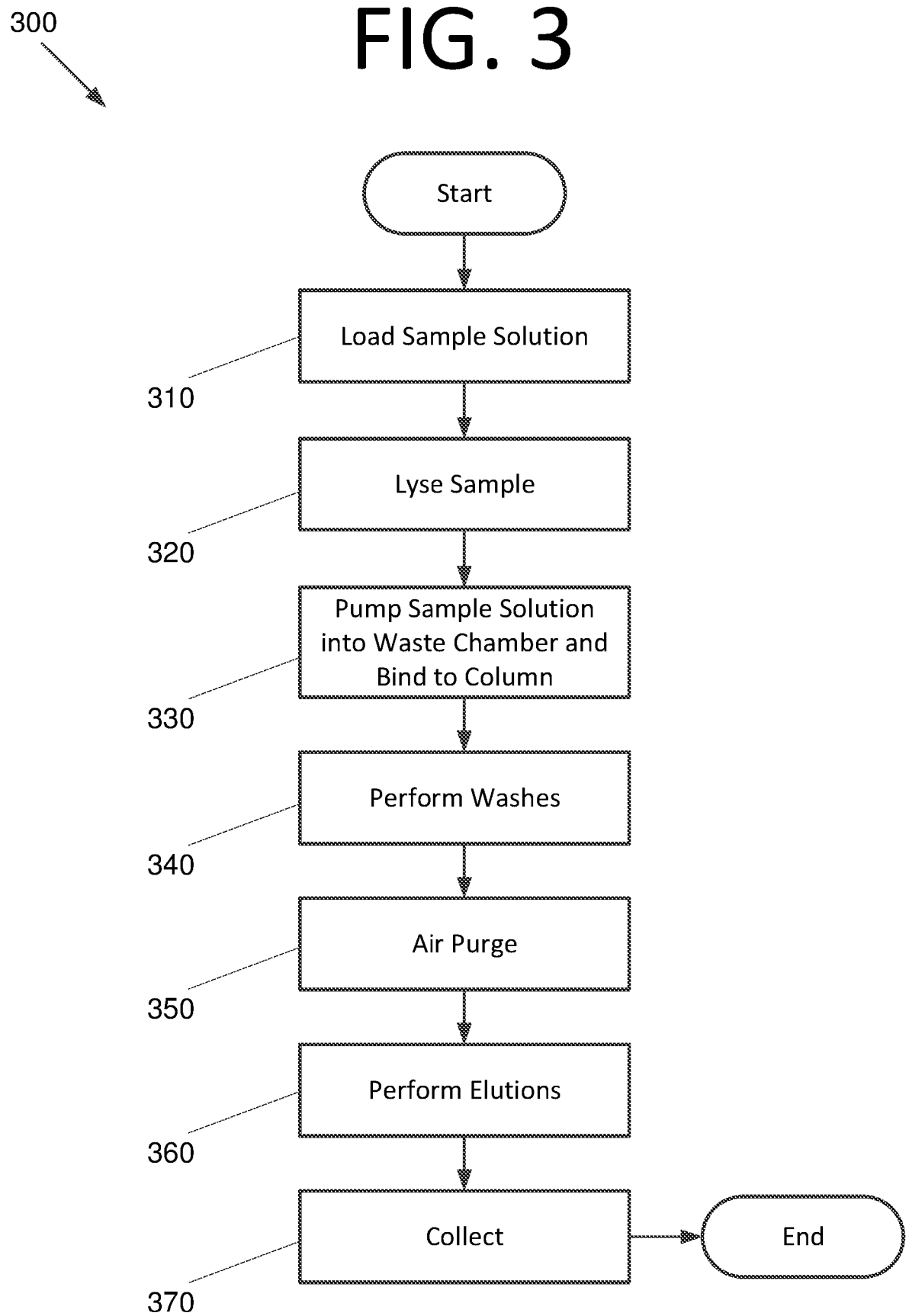
FIG. 3 is a flowchart illustrating a process for extracting nucleic acids from a biological sample via a fully enclosed sample preparation device, according to an embodiment of the present invention.

FIG. 3 is a flowchart 300 illustrating a process for extracting nucleic acids from a biological sample via a fully enclosed sample preparation device, according to an embodiment of the present invention. The process begins with pumping a solution containing the biological sample and a binding buffer into a lysis chamber at 310. For instance, for mammalian samples, the solution may include 400 uL of a suitable binding buffer, such as 5× Claremont Bio™ binding buffer (CBBB), 20 uL Proteinase K, and 20 uL of a reducing agent (e.g., 1M tris(2-carboxyethyl)phosphine (TCEP)). In some embodiments, other reducing agents, such as 2-Mercaptoethanol (BME), dithiothreitol (DTT), etc., may be used. However, these reducing agents may not be as long lasting and may be more toxic. The volume may be increased to 1 mL with 5×CBBB. The sample is then lysed in the lysis chamber at 320 to break down the biological components of the biological sample. This may be accomplished via applying mechanical energy (e.g., vibrational, oscillatory, and/or rotational energy), applying acoustic energy, applying a combination thereof, or applying any other suitable energy or combination of energies without deviating from the scope of the invention. Lysing may be accomplished in some embodiments via beads of a lysing particulate material, such as ceramic, glass, zirconia, zirconia/silica, zirconium silicate, yttria-stabilized zirconia, metal, plastic, nickel, tungsten, tungsten carbide, yttrium stabilized zirconia, sand, and/or particles of any suitable lysing particulate material without deviating from the scope of the invention. The lysing particulate material may have a diameter in the range of 10 to 600 microns in some embodiments.

In some embodiments, the sample solution includes magnetic particles (e.g., 1 μm particles), or these may be added after lysing is performed to facilitate further DNA or RNA capture. The lysed solution is then pumped from the lysis chamber through a nucleic acid extraction column and into a waste chamber at 330. The extraction column contains a particulate material that has an affinity for nucleic acid. As the lysed solution passes over the particulate material, nucleic acids bind to the extraction column. The particulate material of the extraction column may include, but is not limited to, a ceramic, a glass, a zirconia, a silica, a sand, a metal core, or any combination thereof coated with a material that facilitates binding of the nucleic acid.

Once the biological material has been lysed, multiple washes are performed at 340 such that the wash buffers are pumped into and out of the lysis chamber, through the nucleic acid extraction column, and into the waste chamber. This removes unbound species to waste. A first wash buffer and a second wash buffer may be used in some embodiments. For instance, the first wash buffer may include a suitable wash buffer, such as 5 ml 1× Claremont Bio™ wash buffer (CBWB), +10 uL proteinase K, +50 uL of 1M TCEP [10 mM]f and the second wash buffer may include 40 ml 1×CBWB+100 uL of 1M TCEP [2.5 mM]f.

In some embodiments, the wash buffer(s) may be low ionic strength zwitterion-containing buffers having a pH between 3 and 6. The wash buffer(s) may include at least one amino acid, at least one aminosulfonic acid, at least one aminocarboxylic acid, or any combination thereof. The at least one zwitterionic substance may have a pKa within a range of 2 to 4. In some embodiments, the buffer(s) are or include a glycine buffer with a pH of approximately 4.

Once the wash buffers have been employed, an air purge is used at 350 to help remove any remaining wash buffer from the system. Multiple elutions are then performed at 360 using elution buffers to properly extract the desired DNA, RNA, or protein, and the desired DNA, RNA, or protein is collected at 370. For instance, in some embodiments, a 0.75 uL high stringency wash (HSW) with a suitable elution buffer, such as 1× Claremont Bio™ elution buffer (CBEB), may first be employed to remove dirty, low molecular weight/degraded RNA (this elution is pumped into the waste chamber). The concentration is relatively high, but the RNA profile shows RNA are lower RIN with high RNases. Alternatively, this elution could be saved for a gel run. A second elution may then be performed with 0.5-1.0 mL of 1×CBEB (pH 8.0). This RNA is much higher quality, with RIN 6.7 to 9. In some embodiments, the elution buffer(s) have a pH of greater than 7, and in certain embodiments, of between 8 and 9.5.

Figure 4:
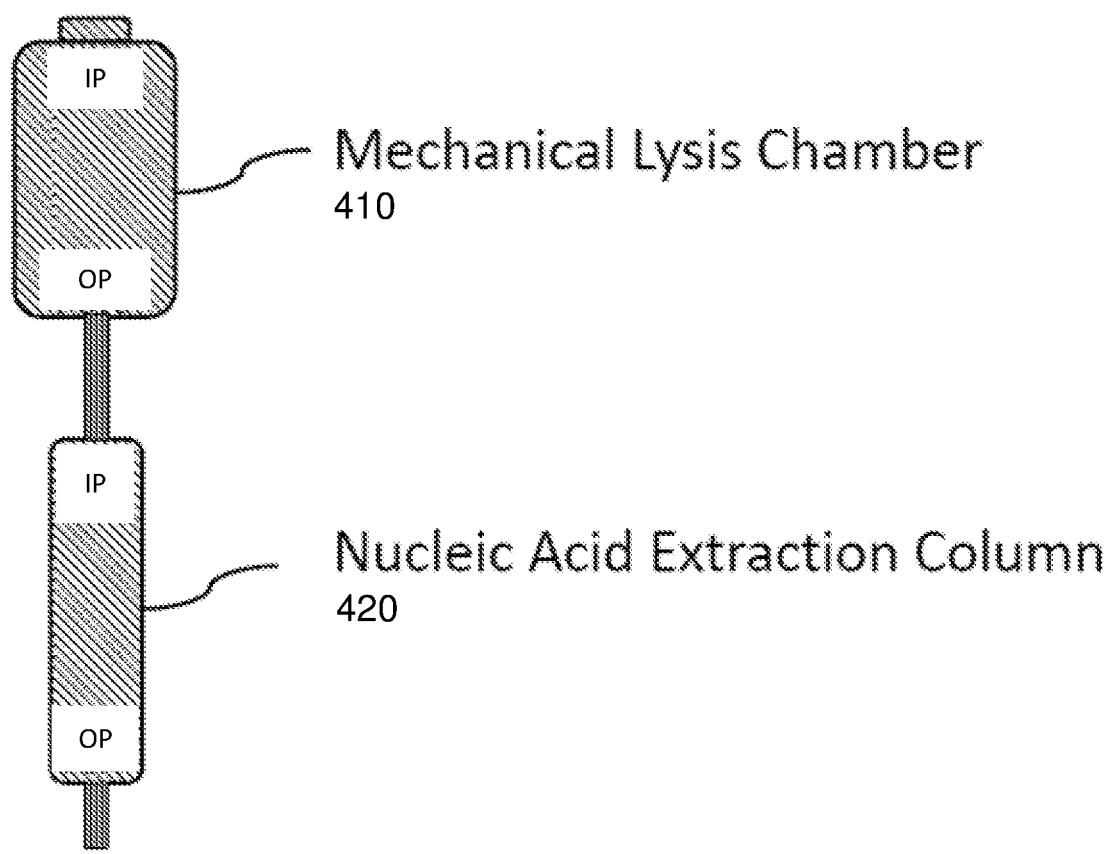
FIG. 4 is an architectural diagram illustrating a sample preparation device, according to an embodiment of the present invention.

FIG. 4 is an architectural diagram illustrating a sample preparation device 400, according to an embodiment of the present invention. Sample preparation device 400 includes a mechanical lysis chamber 410 that contains a particulate lysing material and a nucleic acid extraction column 420 that contains an affinity medium having an affinity for the nucleic acid of interest. An outlet port of mechanical lysis chamber 410 is sealably connected to an inlet port of nucleic acid extraction column 420. In this embodiment, sample preparation device 400 is not fully enclosed and can be used in any environment.

Figure 5:
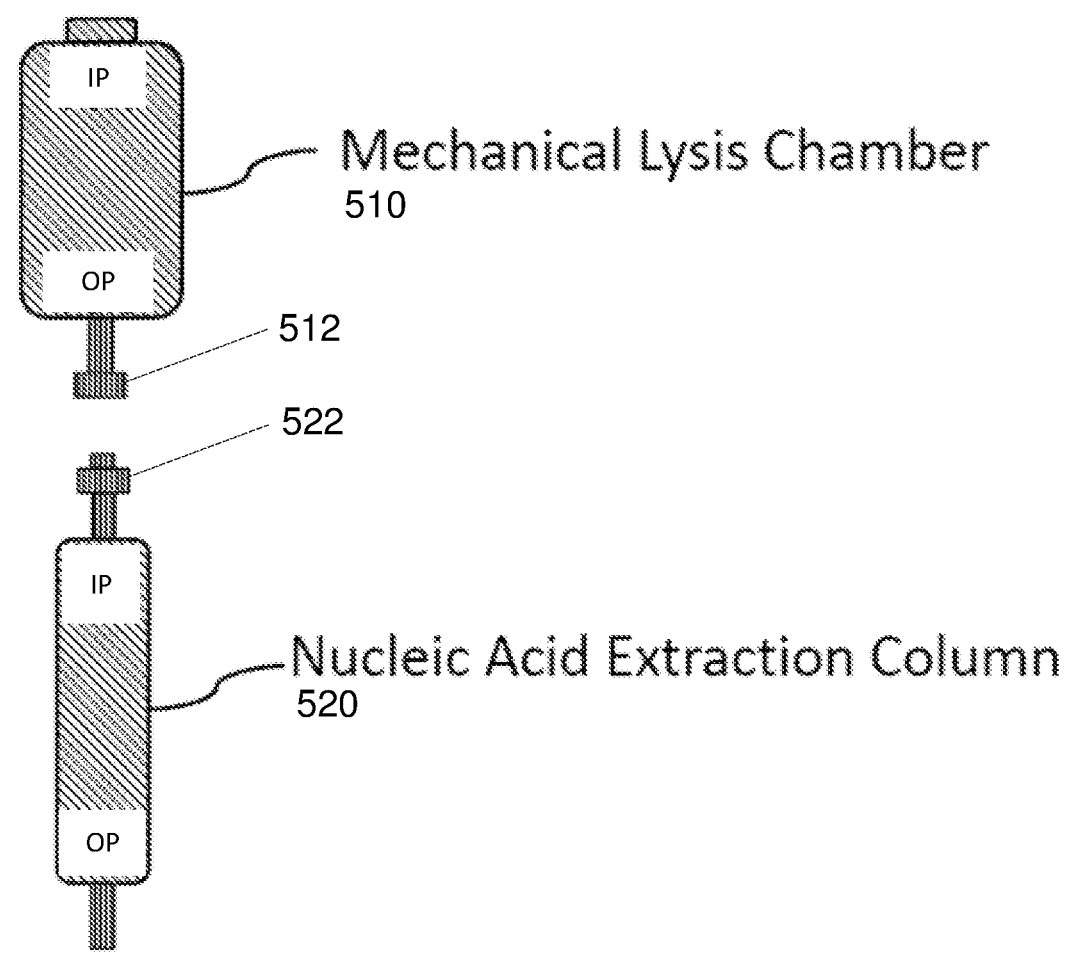
FIG. 5 is an architectural diagram illustrating a sample preparation device, according to an embodiment of the present invention.

FIG. 5 is an architectural diagram illustrating a sample preparation device 500, according to an embodiment of the present invention. Similar to sample preparation device 400, sample preparation device 500 includes a mechanical lysis chamber 510 that contains a particulate lysing material and a nucleic acid extraction column 520 that contains an affinity medium having an affinity for the nucleic acid of interest. However, in this embodiment, mechanical lysis chamber 510 and extraction column 520 are separate, but fitted with connectors 512, 522, respectively. In some embodiments, connectors 512, 522 may be luer-lock connectors that can be sealably connected to one another. Alternatively, mechanical lysis chamber 510 and extraction column 520 may be used serially and need not be connected to one another during use.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A method of extracting and purifying a biological sample using a sample preparation device configured to be used in a microgravity environment, comprising:
    pumping a sample solution comprising a biological sample and a binding buffer into a fully enclosed lysis chamber, the fully enclosed lysis chamber comprising at least one pre-loaded lyophilized reagent, the binding buffer not including a chaotropic salt;
    lysing the sample solution in the fully enclosed lysis chamber to break down biological components of the biological sample;
    pumping the lysed sample solution from the fully enclosed lysis chamber through a fully enclosed extraction column and into a fully enclosed waste chamber, the fully enclosed extraction column comprising an affinity medium, wherein DNA, RNA or protein binds to the affinity medium in the fully enclosed extraction column;
    washing the sample preparation device using at least one wash buffer by pumping the at least one wash buffer into and out of the fully enclosed lysis chamber, through the fully enclosed extraction column, and into the fully enclosed waste chamber, the at least one wash buffer not including alcohol;
    performing at least one elution using at least one elution buffer not comprising an alcohol to properly extract DNA, RNA, or a protein from the fully enclosed extraction column; and
    collecting the extracted DNA, RNA, or protein in a fully enclosed collection chamber,
    wherein the fully enclosed lysis chamber is sealably connected to the fully enclosed extraction column.

2. The method of claim 1, wherein the fully enclosed lysis chamber applies mechanical energy to perform the lysing.

3. The method of claim 1, wherein the fully enclosed lysis chamber comprises beads of a lysing particulate material.

4. The method of claim 3, wherein the beads comprise a ceramic, a glass, zirconia, zirconia/silica, zirconium silicate, yttria-stabilized zirconia, metal, plastic, nickel, tungsten, tungsten carbide, yttrium stabilized zirconia, sand, or any combination thereof.

5. The method of claim 4, wherein the lysing particulate material has a diameter in the range of 10 to 600 microns.

6. The method of claim 1, wherein the sample solution comprises magnetic particles to facilitate biological material capture.

7. The method of claim 1, wherein the fully enclosed extraction column comprises a particulate material that has an affinity for nucleic acid.

8. The method of claim 7, wherein the particulate material of the fully enclosed extraction column comprises a ceramic, a glass, a zirconia, a silica, a sand, a metal core, or any combination thereof, coated with a material that facilitates binding of nucleic acid.

9. The method of claim 1, wherein the at least one wash buffer is a low ionic strength zwitterion-containing buffer comprising at least one zwitterion-containing substance, the zwitterion-containing buffer having a pH between 3 and 6.

10. The method of claim 9, wherein the at least one zwitterionic substance has a pKa within a range of 2 to 4.

11. The method of claim 1, wherein the at least one wash buffer comprises at least one amino acid, at least one aminosulfonic acid, at least one aminocarboxylic acid, or any combination thereof.

12. The method of claim 1, wherein the at least one buffer comprises a glycine buffer with a pH of 4.

13. The method of claim 1, wherein the at least one elution buffer has a pH between 8 and 9.5.

14. A method of using a sample preparation device configured to be used in a microgravity environment, comprising:
    pumping a sample solution comprising a biological sample and a binding buffer into a fully enclosed lysis chamber, the fully enclosed lysis chamber comprising at least one pre-loaded lyophilized regent, the binding buffer not including a chaotropic salt;
    lysing the sample solution in the fully enclosed lysis chamber to break down biological components of the biological sample;
    pumping the lysed sample solution from the fully enclosed lysis chamber through a fully enclosed extraction column and into a fully enclosed waste chamber, binding DNA, RNA or protein to matter in the fully enclosed extraction column; and
    washing the sample preparation device using at least one wash buffer by pumping the at least one wash buffer into and out of the fully enclosed lysis chamber, through the fully enclosed extraction column, and into the fully enclosed waste chamber, the at least one wash buffer not including alcohol,
    wherein the fully enclosed lysis chamber is sealably connected to the fully enclosed extraction column.

15. The method of claim 14, further comprising:
    performing at least one elution using at least one elution buffer to properly extract DNA, RNA, or a protein from the fully enclosed extraction column; and
    collecting the extracted DNA, RNA, or protein.

16. The method of claim 14, wherein the fully enclosed lysis chamber comprises beads of a lysing particulate material, the beads comprising a ceramic, a glass, zirconia, zirconia/silica, zirconium silicate, yttria-stabilized zirconia, metal, plastic, nickel, tungsten, tungsten carbide, yttrium stabilized zirconia, sand, or any combination thereof.

17. The method of claim 14, wherein the fully enclosed extraction column comprises a particulate material that has an affinity for nucleic acid, the particulate material comprising a ceramic, a glass, a zirconia, a silica, a sand, a metal core, or any combination thereof, coated with a material that facilitates binding of nucleic acid.

18. The method of claim 14, wherein the at least one wash buffer is a low ionic strength zwitterion-containing buffer comprising at least one zwitterion-containing substance, the zwitterion-containing buffer having a pH between 3 and 6.

19. A method, comprising:
lysing a sample solution in a fully enclosed lysis chamber of a sample preparation device configured to be used in a microgravity environment to break down biological components of a biological sample comprising a binding buffer, the binding buffer not including a chaotropic salt and the fully enclosed lysis chamber comprising at least one pre-loaded lyophilized reagent; and
washing the sample preparation device using at least one wash buffer by pumping the at least one wash buffer into and out of the fully enclosed lysis chamber, through a fully enclosed extraction column, and into a fully enclosed waste chamber the at least one wash buffer not including alcohol, and
purging the fully enclosed extraction chamber with air to remove any residual at least one wash buffer and pumping the residual at least one wash buffer into the fully enclosed waste chamber,
wherein the fully enclosed lysis chamber is sealably connected to the fully enclosed extraction column.

20. The method of claim 19, further comprising:
performing at least one elution using at least one elution buffer to properly extract DNA, RNA, or a protein from the fully enclosed extraction column; and
collecting the extracted DNA, RNA, or protein.

\* \* \* \* \*